(12) United States Patent
Nurmi

(10) Patent No.: US 7,371,544 B2
(45) Date of Patent: May 13, 2008

(54) HOMOGENOUS METHOD FOR THE DETECTION OF A POLYNUCLEOTIDE, WITH E.G. CLEAVABLE LANTHANIDE CHELATE LABEL

(76) Inventor: Jussi Nurmi, Bodnäsin rantatie 72, Parainen (FI) 21600

( * ) Notice: Subject to any disclaimer, the term of this patent is extended or adjusted under 35 U.S.C. 154(b) by 535 days.

(21) Appl. No.: 10/203,516

(22) PCT Filed: Feb. 13, 2001

(86) PCT No.: PCT/FI01/00128

§ 371 (c)(1),
(2), (4) Date: Aug. 12, 2002

(87) PCT Pub. No.: WO01/61034

PCT Pub. Date: Aug. 23, 2001

(65) Prior Publication Data

US 2004/0029119 A1 Feb. 12, 2004

(30) Foreign Application Priority Data

Feb. 16, 2000 (FI) .................................. 20000333

(51) Int. Cl.
*C12P 19/34* (2006.01)
*C12Q 1/68* (2006.01)
(52) U.S. Cl. ........................................ 435/91.2; 435/6
(58) Field of Classification Search .................... 435/6, 435/18, 91.1; 436/800; 536/24.3; 935/77, 935/78
See application file for complete search history.

(56) References Cited

U.S. PATENT DOCUMENTS 4,922,733 A * 5/1990 Driesen et al. ........... 68/205 R

| 5,210,015 | A | 5/1993 | Gelfand et al. |
| 5,256,535 | A | 10/1993 | Ylikoski et al. |
| 5,487,972 | A | 1/1996 | Gelfand et al. |
| 5,538,848 | A | 7/1996 | Livak et al. |
| 5,658,737 | A * | 8/1997 | Nelson et al. ................ 435/6 |
| 5,786,139 | A | 7/1998 | Burke et al. |

(Continued)

FOREIGN PATENT DOCUMENTS

EP 0 070 685 A2 1/1983

(Continued)

OTHER PUBLICATIONS

Syvanen et al. Nucleic Acid Research, 1986, vol. 14(2), p. 1017-1028.*

(Continued)

*Primary Examiner*—Kenneth R. Horlick
*Assistant Examiner*—Molly Baughman
(74) *Attorney, Agent, or Firm*—Rothwell, Figg, Ernst & Manbeck p.c.

(57) ABSTRACT

The present invention relates to a homogenous method for detecting at least one target polynucleotide in a sample comprising the steps of
contacting a sample comprising said polynucleotide or polynucleotide forming nucleic acids or derivatives thereof, with labelled oligonucleotide probe under conditions where said oligonucleotide probe selectively hybridizes to said target polynucleotide, wherein the signal of the label increases or decreases upon the hybridization between the oligonucleotide probe and the target polynucleotide,
exciting the label, and
monitoring the signal intensity of said label to indicate the presence or absence in a sample of said target polynucleotide.
According to the invention, said label is measured by time resolved fluorometry.

13 Claims, 8 Drawing Sheets

U.S. PATENT DOCUMENTS

| | | | |
|---|---|---|---|
| 5,827,653 | A | 10/1998 | Sammes et al. |
| 5,853,990 | A * | 12/1998 | Winger et al. .................. 435/6 |
| 5,854,008 | A * | 12/1998 | Diamandis ................. 435/7.91 |
| 5,925,517 | A | 7/1999 | Tyagi et al. |
| 5,948,899 | A | 9/1999 | Arnold, Jr. et al. |
| 5,952,202 | A * | 9/1999 | Aoyagi et al. ............. 435/91.2 |
| 5,998,146 | A * | 12/1999 | Latva et al. .................... 435/6 |
| 6,004,745 | A | 12/1999 | Arnold, Jr. et al. |
| 6,150,097 | A | 11/2000 | Tyagi et al. |
| 6,635,427 | B2 * | 10/2003 | Wittwer et al. ................. 435/6 |

FOREIGN PATENT DOCUMENTS

| | | |
|---|---|---|
| EP | 0103558 | 3/1984 |
| EP | 0 232 967 A2 | 8/1987 |
| EP | 0403593 | 12/1990 |
| EP | 0 601 889 A2 | 6/1994 |
| EP | 0639647 | 2/1995 |
| EP | 0 770 610 A1 | 5/1997 |
| EP | 0770610 | 5/1997 |
| EP | 0930370 | 7/1999 |
| FI | 88545 | 3/1991 |
| WO | WO 98/04738 | 2/1998 |
| WO | WO 98/15830 | 4/1998 |
| WO | WO 00/05409 | 2/2000 |
| WO | WO 01/88195 A1 | 11/2001 |

OTHER PUBLICATIONS

Chemical Abstracts, 120:134215, Mukkala, V.M. et al., "Development of Luminescent Europium (III) and Terbium (III) Chelates of 2,2':6',2"-Terpyridine Derivatives for Protein Labeling," *Helv. Chim. Acta* (1993), 76(3), 1361-78.

Chemical Abstracts, 126:324504, Takalo, H. et al., "Development of Luminescent Terbium (III) Chelates for Protein Labeling. Effect of Triplet-State Energy Level," *Helv. Chim. Acta* (1997), 80(2) 372-387.

Biosis Abstract, 200100102763, Nurmi, J. et al., "Time-Resolved Fluorometry in End-Point and Real-Time PCR Quantification of Nucleic Acids," *Luminescence* (2000), 15(6), 381-88.

Nurmi, J. et al. (2000). "A new label technology for the detection of specific polymerase chain reaction products in a closed tube," *Nucl. Acids Res.* 28(8):i-vi.

Latva, M. et al., "Correlation between the lowest triplet state energy level of the ligand and lanthanide (III) luminescence quantum yield," Journal of Luminescence, 75:149-169, 1997.

Lövgren, T., "Sensitive bioaffinity assays with individual microparticles and time-resolved fluorometry," Clinical Chemistry, 43(10):1937-1943, 1997.

Mukkala, V. et al., "Development of luminescent Europium(III) and Terbium(III) Chelates of 2,2':6',2"-Terpyridine derivatives for protein labeling," Helvetica Chimica Acta, 76: 1361-1378, 1993.

Nurmi, J. et al., "Time-resolved fluorometry in end-point and real-time PCR quantification of nucleic acids," Luminescence, 15:381-388, 2000.

Takalo, H. et al., "Development of luminescent Terbium(III) Chelates for protein labelling:effect of triplet-state energy level," Helvetica Chimica Acta, 80:372-387, 1997.

* cited by examiner

SEQUENCE LISTING

<160> NUMBER OF SEQ ID NOS: 6

<210> SEQ ID NO 1
<211> LENGTH: 21
<212> TYPE: DNA
<213> ORGANISM: Artificial
<220> FEATURE:
<223> OTHER INFORMATION: oligonucleotide primer

<400> SEQUENCE: 1
tgaaccagag gagttcttga c                                              21

<210> SEQ ID NO 2
<211> LENGTH: 19
<212> TYPE: DNA
<213> ORGANISM: Artificial
<220> FEATURE:
<223> OTHER INFORMATION: oligonucleotide primer

<400> SEQUENCE: 2
cccagaatca cccgagcag                                                 19

<210> SEQ ID NO 3
<211> LENGTH: 24
<212> TYPE: DNA
<213> ORGANISM: Artificial

-continued

```
<220> FEATURE:
<223> OTHER INFORMATION: probe

<400> SEQUENCE: 3
ccttctgagg gtgaacttgc gctg                                              24

<210> SEQ ID NO 4
<211> LENGTH: 24
<212> TYPE: DNA
<213> ORGANISM: Artificial
<220> FEATURE:
<223> OTHER INFORMATION: probe

<400> SEQUENCE: 4
ccttctgagg gtgattgcgc actg                                              24

<210> SEQ ID NO 5
<211> LENGTH: 22
<212> TYPE: DNA
<213> ORGANISM: Artificial
<220> FEATURE:
<223> OTHER INFORMATION: probe

<400> SEQUENCE: 5
ccttctgagg gtgaacttgc gc                                                22

<210> SEQ ID NO 6
<211> LENGTH: 22
<212> TYPE: DNA
<213> ORGANISM: Artificial
<220> FEATURE:
<223> OTHER INFORMATION: target oligonucleotide

<400> SEQUENCE: 6
gcgcaagttc accctcagaa gg                                                22
```

HOMOGENOUS METHOD FOR THE DETECTION OF A POLYNUCLEOTIDE, WITH E.G. CLEAVABLE LANTHANIDE CHELATE LABEL

CROSS-REFERENCE TO RELATED APPLICATIONS

The present application is a national stage filing under 35 U.S.C. §371 of PCT/FI01/00128 filed on 13 Feb. 2001 and claims priority under 35 U.S.C. §119 to Finland patent application No. 20000333 filed on 16 Feb. 2000.

The present invention relates to a homogenous method for the detection of a polynucleotide by using an oligonucleotide probe labelled with an environment sensitive label.

BACKGROUND OF THE INVENTION

The publications and other materials used herein to illuminate the background of the invention, and in particular, cases to provide additional details respecting the practice, are incorporated by reference.

The polymerase chain reaction (PCR) (Saiki et al., 1985) is by far the most important nucleic acid diagnostic tool. The first diagnostic tests based on PCR were quite cumbersome and not amenable to large scale screening methods (Isaksson et Landegren, 1999). Several post PCR steps, such as restriction enzyme analysis, agarose gel electrophoresis or heterogeneous hybridization assays were needed to confirm the identity of the PCR product (Kricka, 1999). Recently, the development of new fluorescent techniques has, however, led to novel assay formats that greatly simplify the protocols used for the detection of specific nucleic acid sequences. These methods involve the detection of a specific PCR product in a homogeneous solution without the need to open the amplification tubes after PCR (Williams et al., 1998). The results can be read in real time as the PCR product is accumulated or at the end of the thermal cycling protocol directly from the amplification wells. The choice between real time or end point measurement modes depends on whether a quantitative or qualitative assay is desired.

At the moment four technologies enabling specific sequence detection in a closed tube are commercially available. All of them (the TaqMan, Molecular Beacons, LightCycler and Amplifluor technologies) are based on fluorescence resonance energy transfer (FRET) (Clegg, 1992; Selvin, 1995). TaqMan (Holland et al. 1991; Lee et al., 1993) uses a linear probe that has a FRET donor in its 5' end and an acceptor moiety at the 3' end (Livak et al., 1995). When the probe is single stranded, the three dimensional conformation of the probe brings the two labels close enough to each other for the acceptor to quench the donor fluorescence. As the probe hybridizes to its target or when a DNA polymerase that has a 5' to 3' exonuclease activity cleaves it, the distance between the two labels increases enough for the donor fluorescence intensity to increase markedly. The difference between TaqMan probes and molecular beacons (Tyagi et Kramer, 1996) is that the optimized stem-loop structure of molecular beacons brings the two labels as close together as possible when the probe is not hybridized to a target sequence. This ensures maximal quenching efficiency. Upon hybridization to a target (or when cleaved by a DNA polymerase), the fluorescence intensity of the FRET donor increases as the physical contact between the two labels is disrupted. The Amplifluor technology (Nazarenko et al., 1997) utilizes hairpin shaped primers that basically function the same way molecular beacons do: when the primer is incorporated into a PCR product, the donor and quencher moieties are separated and donor fluorescence is thus increased. The Hybridization Probe format (Morrison, 1995) used in the LightCycler system (Wittwer et al, 1997a; Wittwer et al, 1997b) uses two adjacent probes that are labeled such that when both probes are hybridized to a target, the labels are brought close to each other and a FRET occurs between them. The sensitized acceptor emission is measured instead of the donor fluorescence.

All of these methods based on FRET are characterized by relatively high signal-to-noise ratios and a good ability to discriminate between positive and negative reactions. However, they are all limited in the sense that either a dual label probe or primer or two separate probes per each target have to be used. This seriously complicates probe design and synthesis. In addition, since they all employ labels with rapidly decaying fluorescence and broad emission peaks, the possibilities for multiplex detection are limited.

The two labels used in the homogenous assays described above are of different kind, i.e. one of the labels shall quench the other label as long as the probe to which they are attached is non-hybridized.

OBJECTS AND SUMMARY OF THE INVENTION

The object of the present invention is to provide a novel homogenous method for the detection of polynucleotides, wherein the oligonucleotide probe can be labelled with one single label. The signal of said label itself should be highly dependent on whether or not the probe is hybridized, and therefore, the need for another counteracting label on the probe should be eliminated.

Thus, the present invention relates to a homogenous method for detecting at least one target polynucleotide in a sample comprising the steps of contacting a sample comprising said polynucleotide or polynucleotide forming nucleic acids or derivatives thereof, with labelled oligonucleotide probe under conditions where said oligonucleotide probe selectively hybridizes to said target polynucleotide, wherein the signal of the label increases or decreases upon the hybridization between the oligonucleotide probe and the target polynucleotide, exciting the label, and monitoring the signal intensity of said label to indicate the presence or absence in a sample of said target polynucleotide.

According to the invention, said label is measured by time resolved fluorometry.

BRIEF DESCRIPTION OF THE DRAWINGS

FIG. 2A: Background subtracted terbium fluorescence of reactions containing no template (NTC), 10,000 molecules of PSA or 10,000 molecules of mPSA cDNA template before addition of POPO™-3. Black and grey columns denote reactions containing a PSA or MPSA specific probe, respectively. FIG. 2B: Fluorescence intensity ratios after addition of POPO™-3. When PSA is used as template, the PSA specific probe (black column) is cleaved and thus the addition of POPO™-3 does not affect the terbium signal at 545 nm. Accordingly, the sensitized POPO™-3 emission at 572 nm is less significant than in negative reactions. The result is the same, when mPSA is used as template in an amplification reaction containing a mPSA specific probe (grey column).

FIGS. 8A, 8B, 8C and 8D show the terbium and europium signal-to-noise ratios in reactions containing no template (A), $5*10^5$ molecules of PSA double stranded cDNA (B), $5*10^5$ molecules of mPSA (C) or $5*10^5$ molecules of PSA and $5*10^5$ molecules of mPSA (D). The europium signals have been corrected for terbium background by subtracting from the signals measured at 615 nm the terbium signal of the same cycle*0.24. The signals have been transformed to signal-to-noise ratios by dividing each fluorescence signal by the average fluorescence at the same wavelength in cycles 6 to 10. The terbium signal rises above background only in the presence of a complementary PSA target and the europium signal in the presence of a complementary mPSA target.

DETAILED DESCRIPTION OF THE INVENTION

Figure 1:
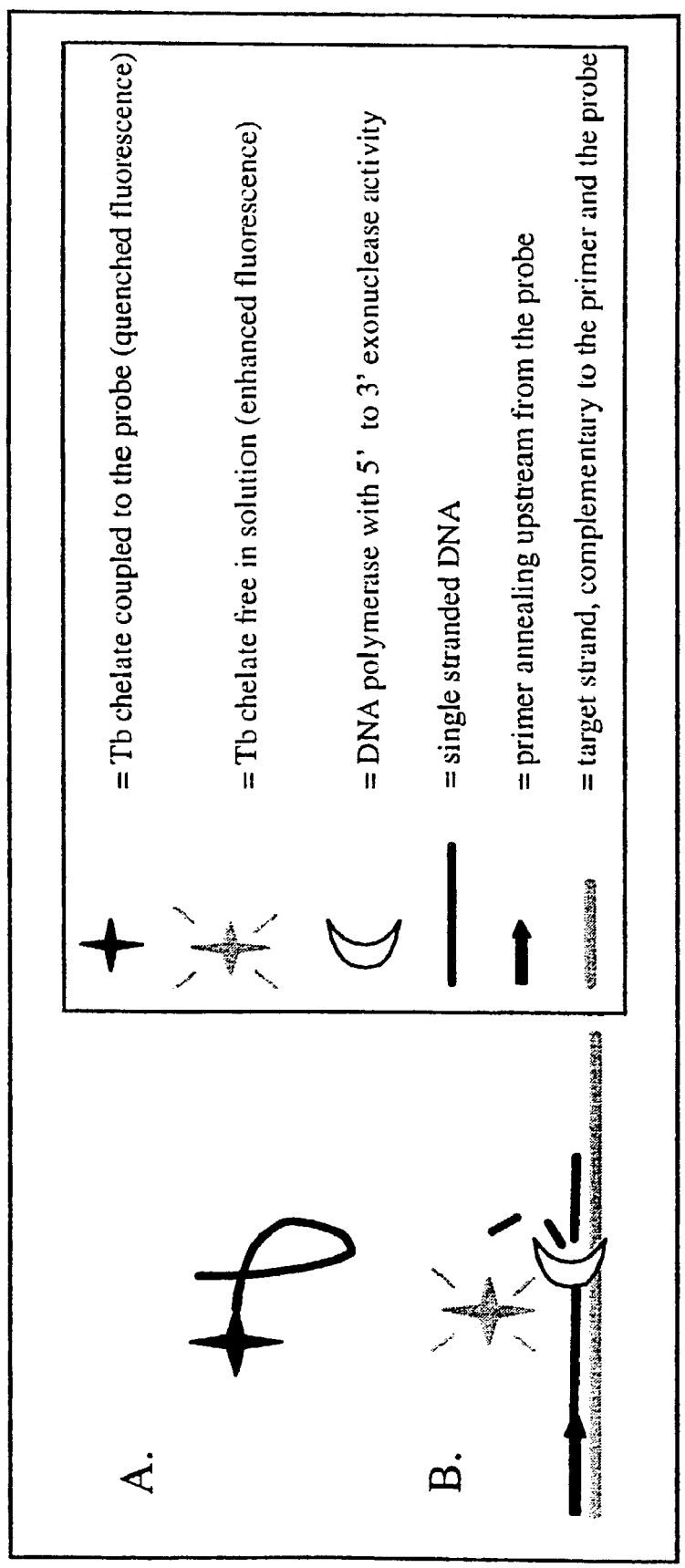
FIG. 1 shows the assay principle. A: When the stable, fluorescent terbium chelate used as label is coupled to a single stranded stretch of DNA, the fluorescence intensity of the chelate is significantly lower than when the chelate is free in solution. B: Hybridization of a probe labeled at its 5' end with the chelate to a complementary target amplicon during the annealing/extension step of PCR results in detachment of the label from the probe and a subsequent signal increase. This detachment is catalyzed by the 5' to 3' exonuclease activity of the DNA polymerase that is used to amplify the target sequence.

In time-resolved fluorometry, the emission intensity of a sample is measured after single, consecutive excitation pulses. The excitation flash time is typically 1 to 10 μs. Emission is measured with a photomultiplier tube by photon counting. After a certain delay from excitation, photon counting is initiated by electronic gating. The flash frequency, the total measurement time as well as the delay and counting times can be varied, but normally the total measurement time is 1 or 2 s comprising 1000 individual cycles during which the total photon amount is counted. Time-resolved fluorometry is widely used in bioaffinity assays together with labels having a long decay time (Lovgren et Pettersson, 1990).

In the present invention, time-resolved fluorometry is used to measure the emission intensities of environment sensitive labels having a long decay time. These labels do not need any counteracting labels in order to distinguish the signals from a hybridized and a non-hybridized probe. Such labels are typically stable fluorescent lanthanide chelates with a long decay time. These chelates contain a light-absorbing group that is sensitive to its immediate chemical environment. The lanthanide is most preferably terbium or europium. Such chelates are disclosed in the literature (Latva et al., 1997; Mukkala et al., 1993; Takalo et al., 1997). Especially preferable labels are, for example, terbium or europium chelates of a derivative of 2,2',2",2'''-{[6,6'-(Pyrazole-1",3"-diyl)bis(pyridine)-2,2'-diyl]bis(methyl-enenitrilo)} tetrakis (acetic acid) (Latva et al., 1997; Takalo et al., 1997), and 2,2':6',2"-terpyridine (Mukkala et al., 1993; Takalo et al., 1997).

The environment-sensitivity of a luminescent lanthanide chelate can be detected as a measurable change in the chelate's luminescent properties when the immediate chemical environment of the chelate changes. When the time resolved fluorescence intensity is monitored using constant measurement parameters (such as excitation and emission wavelengths, excitation energy level, delay time, measurement window time and cycle time), then, depending on the situation, the change is an increase or a decrease in signal. If, for example, the linkers between the label moiety and the probe oligonucleotide expose the label to fewer water molecules when the probe is not hybridized than when the probe is hybridized, then the signal intensity may decrease upon hybridization. Vice versa, in a different situation, the probe structure can be such that the label signal is increased upon hybridization, because the label is better shielded from quenching agents when the probe is hybridized to a complementary target sequence.

If the label is cleaved from the probe as a result of hybridization, the difference in signal strenght (compared to the signal from the non-hybridized probe) is still enhanced. The cleavage can be carried out chemically, e.g. by an enzymatic reaction.

According to one embodiment, the sample is contacted with several oligonucleotide probes having different base sequences, wherein said probes are labelled so that all labels have distinguishable signal wavelengths. The different oligonucleotide probes have different base sequences so as to hybridize to different target polynucleotides in the sample.

The oligonucleotide probe can also, although it is not necessary, include a quencher molecule that quenches the signal of the label as long as said probe is non-hybridized.

The method can be carried out in the real-time monitoring of nucleic acid synthesis reactions by measuring the signal intensity of the label at regular intervals during a nucleic acid synthesis reaction and comparing the signal intensities of a reaction containing a sample of nucleic acids and of a negative control reaction that does not contain said target polynucleotide. A difference in the signal intensities of these two indicates the presence of the target polynucleotide in the sample. The point of time when the signal intensity of a reaction containing the target polynucleotide clearly starts to differ from the signal intensity of the negative control reaction is detected. The detected point of time indicates the initial amount of the target polynucleotide in the sample.

According to another alternative, the method can be carried out in the end-point detection of nucleic acid synthesis reaction products by measuring the signal intensity of the label after the nucleic acid synthesis reaction and comparing the signal intensity of a reaction containing the sample of nucleic acids and the signal intensity of a negative control reaction that does not contain the target polynucleotide. A difference in the signal intensities of these reactions indicates the presence of the target polynucleotide in the sample of nucleic acids.

The oligonucleotide probe can, for example, be made of DNA, RNA or any nucleic acid derivative such as peptide nucleic acid (PNA), or the oligonucleotide probe is a chimera of any two or more different kinds of nucleic acids or derivatives thereof.

The target polynucleotide can, for example, be a single stranded nucleic acid, DNA or RNA or a derivative thereof, or a double stranded stretch of DNA or RNA or a derivative thereof or a hybrid of DNA and RNA or of DNA or RNA and a nucleic acid derivative such as PNA.

The method can, for example, be an assay where the label is released from the oligonucleotide probe by the 5' to 3' exonuclease activity of a nucleic acid polymerase.

According to another alternative, the method can be an assay where the oligonucleotide probe comprises RNA bases and is cleaved by ribonuclease H when hybridized to a single stranded target DNA.

The label can, for example, be attached to the 5' terminal nucleotide, the 3' terminal nucleotide, to the 5' and 3' terminal nucleotides of the oligonucleotide probe, or to any nucleotide of the oligonucleotide probe between 5' and 3' terminal nucleotides.

In the following Experimental Section, Study I, we present a novel method for the qualitative and quantitative detection of a specific nucleic acid sequence in a homogeneous solution that relies on the 5' exonuclease activity of a nucleic acid polymerase and on the use of a stable, fluorescent terbium chelate (FIG. 1). The fluorescence intensity of this chelate is greatly affected by the immediate chemical environment of the label. The chelate in Study I and Study III is coupled to the 5' end of an oligonucleotide probe that is used to monitor PCR amplification of a complementary target in a closed tube. An increase in lanthanide fluorescence is seen as the DNA polymerase detaches the label from the probe hybridized downstream from a primer oligonucleotide. There are two main differences between this assay and conventional TaqMan 5' exonuclease assays.

Firstly, there is no need for a quencher moiety in the probe. Secondly, because of the possibility to do the measurements in a time-resolved manner, this label technology can easily be combined with conventional, prompt labels in order to make a multiplex assay without the need to rely on any spectral resolution software. In Study I we describe the environment dependent fluorescent properties of an environment sensitive Tb chelate and demonstrate the applicability of this technology to qualitative and quantitative detection of specific target sequences. The feasibility of multi-analyte assays combining environment sensitive lanthanide chelates with conventional TaqMan detection is also shown here.

We also demonstrate the use of these chelates in homogenous hybridizations where signal increase is not dependent on probe cleavage (Study II). Moreover, we present a study of multiplex detection of two different target nucleic acids using probes labelled with europium and terbium (Study III).

EXPERIMENTAL SECTION

Study I

Oligonucleotides and PCR templates: Oligonucleotide primers and probes (table 1) were synthesized on an ABI392 DNA/RNA Synthesizer (PE Applied Biosystems, USA) using standard phosphoramidite chemistry, except for the conventional prostate specific antigen (PSA) cDNA specific TaqMan probe that was purchased from SGS DNA, Sweden. Primary amino groups were introduced to the 5' ends of the probes using an amino modified cytosine phosphoramidite (modC, PerkinElmer Life Sciences, formerly EG&G Wallac, Finland). Two bases that do not hybridize with the target sequence were added to the 3' ends of the probes to make sure that the probes cannot act as primers during PCR.

PSA and mutant PSA (mPSA) specific probes were labeled with a 100-fold molar excess of an isothiocyanate modified stable, fluorescent terbium chelate (2,2',2'',2'''-{{6, 6'-{4''-[2-(4-isothiocyanatophenyl)ethyl]-1H-pyrazole-1'', 3''-diyl}bis(pyridine)-2,2'-diyl} bis-(methylenenitrilo)}tetrakis(acetato) terbium(III); PerkinElmer Life Sciences) by dissolving the chelate and the DNA in 50 mM sodium carbonate buffer (pH 9.8). The DNA concentration was adjusted to about 2 µg µl$^{-1}$ and the reactions were incubated at 37° C. over night. Excess chelate was removed using a Nick gel filtration column (Pharmacia Biotech, Sweden). The probes were HPLC purified using a Sephasil Peptide C8 4.6/100 column (Pharmacia Biotech) and a 16.5 min linear gradient of 2-70% acetonitrile in 50 mM triethylammonium acetate buffer (pH 6.8). The probes were vacuum dried (Hetovac, Heto Holten, Denmark), dissolved in 50 mM Tris-HCl (pH 7.5), quantified spectrophotometrically and stored in small aliquots at −20° C.

PSA and mPSA double stranded cDNAs excised from plasmids pGEM3-PSA and pGEM3-IS (Lundwall et Lilja, 1987; Ylikoski et al., 1999) were used as templates during the development of the technology. Mutant PSA is used as an internal standard in a quantitative PSA reverse transcription PCR assay (Ylikoski et al., 1999). It differs from PSA by a two base-pair deletion that is situated in the middle of the amplicon. Therefore, PSA and mPSA are good model analytes for a detection system that is to be applied to quantitative and qualitative sequence analysis. The template concentrations of stock solutions were determined spectrophotometrically at 260 nm. In the dual end point assay the templates were mixed with a $10^8$-fold excess of human genomic DNA from a healthy donor.

TABLE 1

Oligonucleotides used in this study.

| Oligonucleotide | Sequence from 5' to 3' end[a] (SEQ ID NO:) | Label/position | Nucleotide position |
|---|---|---|---|
| 5' primer | TGA ACC AGA GGA GTT CTT GAC (1) | None | 523-543 |
| 3' primer | MCCC AGA ATC ACC CGA GCA G (2) | None | 667-685 |
| PSA specic Tb probe | MCCT TCT GAG GGT GAA CTT GCG CTG[b] (3) | Tb/5' | 596-617 |
| mPSA specific Tb probe | MCCT TCT GAG GGT GAT TGC GCA CTG[b] (4) | Tb/5' | 594-601, 604-617 |
| PSA specific Taqman probe | CCT TCT GAG GGT GAA CTT GCG C (5) | FAM[c]/5' and TAMRA[d]/3' | 596-617 |

[a]M, amino modified cytosine
[b]bold letters denote bases that are not complementary to the target
[c]FAM, carboxyfluorescein
[d]TAMRA, tetramethylrhodamine Characterization of the fluorescent properties of the probes In order to investigate the effect of probe cleavage on terbium signal intensity, $10^{12}$ molecules of Tb labeled PSA or mPSA probes were cleaved with 25 U of Benzon nuclease (Merck, Germany). The probes were incubated with the enzyme in 50 μl of 50 mM Tris-HCl (pH 7.5) containing 1 mM $MgCl_2$ at 37° C. for 30 min, after which the terbium signals were measured using a Victor™ 1420 Multilabel Counter (PerkinElmer Life Sciences) and compared to signals obtained from intact probes. The following settings were used in all terbium measurements in this study: excitation filter 340 nm; emission filter 545 nm; delay 500 μs; window time 1400 μs and cycle 2000 μs.

To confirm that the probes are in fact cleaved during PCR, PSA and mPSA double stranded cDNAs were amplified in 10 mM Tris-HCl, pH 8.3; 50 mM KCl; 3.5 mM $MgCl_2$; 0.1 mM dNTP:s (Pharmacia Biotech); 0.1 μM 3' primer; 0.2 μM 5' primer; 33 nM PSA or mPSA terbium probe and 1.25 U of AmpliTaq Gold DNA Polymerase (PE Applied Biosystems). Each 50 μl reaction contained 10,000 copies of either PSA or mPSA template or no template at all. The thermal cycling consisted of a 10 min initial denaturation and polymerase activation step at 95° C. followed by 40 cycles of 15 s at 95° C. and 1 min at 61.5° C. The reactions were done in a PTC-200 DNA Engine (MJ Research Inc., USA) in black polypropylene wells (cat. no. 6885, Corning Costar, Great Britain) and sealed with Cycleseal® PCR Plate Sealer (Robbins Scientific Corporation, USA). The terbium signals were measured directly from the amplification wells after thermal cycling at room temperature. To confirm that the detected terbium signal increase in positive reactions was due to probe cleavage, POPO™-3 iodide DNA binding dye (Molecular Probes, USA) was added in each well to a concentration of 100 nM. Time resolved Tb and POPO™-3 iodide emissions at 545 nm and 572 nm were measured. In the measurement at 572 nm, the following settings were used: excitation filter 340 nm; emission filter 572 nm; delay 60 μs; window time 100 μs and cycle 1000 μs. POPO™-3 iodide is excited at terbium's maximum emission wavelength (545 nm) and emits at 570 nm. The binding of POPO™-3 iodide to a terbium labeled probe will therefore result in a fluorescence resonance energy transfer (FRET) between Tb and the dye (Morrison, 1995). This can be seen as a decrease in Tb emission at 545 nm and, on the other hand, as an increase in POPO™-3's sensitized emission, which can be recorded at 572 nm. If the probe has been cleaved, however, there will be no detectable energy transfer between the two fluorophores.

Real Time Quantitative PCR

To demonstrate the quantitative nature of terbium signal generation during thermal cycling, PSA and mPSA were amplified so that the amount of starting template was varied from 0 to $10^7$ molecules. The thermal cycling parameters were as described above. Real time quantitative PCR was performed on a prototype instrument that consisted of a Victor™ 1420 Multilabel Counter measurement unit coupled to a PTC-100 thermal cycler (MJ Research Inc.) through an in house hot lid that was kept at 105° C. The terbium signals were measured at the end of each annealing/extension step to determine the threshold cycles ($C_t$) of individual reactions. The threshold cycle is defined as the PCR cycle where the fluorescence signal-to-noise ratio (S/N) of a given amplification reaction exceeds the threshold S/N value. This threshold value is set by the user. In this study, threshold values of 1.3 for the PSA and 1.35 for the mPSA assay were used. PSA and mPSA standard curves were made by plotting the threshold cycle as a function of initial PSA or mPSA starting copy number.

Dual Assay Using Time Resolved and Prompt Fluorescence 1000 molecules of PSA and/or mPSA double stranded CDNA were amplified in the presence of 250 ng human genomic DNA. Human genomic DNA is not amplified in this assay since the primer sequences represent exon-intron junctions (Ylikoski et al., 1999). The reaction conditions were identical to those used in the real time quantitative PCR, only this time two probes, the PSA specific TaqMan probe and the mPSA specific terbium probe were used, both at a concentration of 33 nM. The FAM and terbium signals were measured directly from the amplification wells after thermal cycling with a Victor™ 1420 Multilabel Counter at room temperature. In the FAM measurement, 485 nm excitation and 535 nm emission filters were used. Excitation energy was set at 24064 and measurement time was 1.0 s. The results were analyzed by calculating the average signals (M) and standard deviation (SD) from reactions containing only genomic DNA and no specific template. A threshold value was set at M+2*SD. All reactions with a terbium or FAM signal greater than the threshold were considered positive for the corresponding template.

Results

Fluorescent Properties of The Terbium Chelate

It has been noted in our laboratory that the fluorescence intensity of the fluorescent terbium chelate 2,2',2'',2'''-{{6,6'-{4''-[2-(4-isothiocyanatophenyl)ethyl]-1H-pyrazole-1'', 3'''-diyl}bis(pyridine)-2,2'-diyl}bis(methylenenitrilo)} tetrakis(acetato) terbium(III) is very sensitive to the immediate chemical environment of the label moiety. Therefore, it was envisioned that detachment of the chelate from a DNA probe would result in a detectable change in terbium fluorescence. By placing the label at the 5' end of a probe, the 5' to 3' exonuclease activity of a thermostable DNA polymerase could be used to detach the chelate from a probe hybridized downstream from a primer during the annealing/extension step of PCR. The resulting signal change could be used to monitor nucleic acid amplification. The idea was first tested by digesting the probe with a nuclease. Enzymatic cleavage of terbium labeled probes resulted in an approximately 3 to 4 fold terbium signal increase (2.9 for the PSA and 3.8 for the mPSA specific probe) when compared to an intact probe.

Figure 2A:
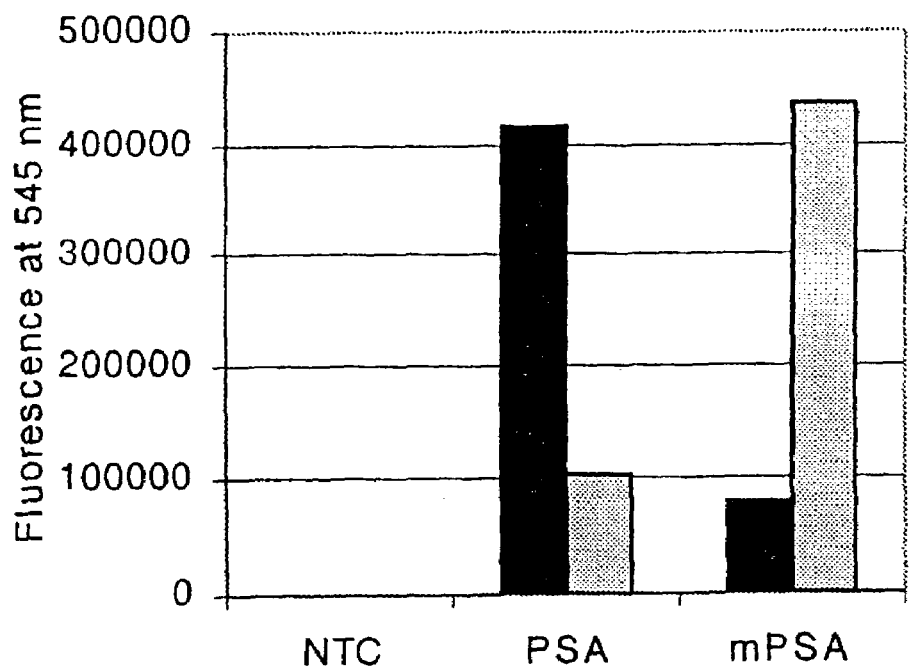
FIGS. 2A and 2B demonstrate homogeneous end point detection of PSA and mPSA amplification.

FIG. 2A illustrates how amplification of a target sequence in the presence of a complementary probe results in a clear terbium signal increase. After 40 cycles, terbium fluorescence is clearly greater in reactions containing a PSA specific probe and 10,000 initial copies of PSA cDNA than in reactions containing no template or a non-specific mPSA template. Accordingly, in reactions containing a mPSA specific probe, only mPSA amplification results in a significant signal increase.

Figure 2B:
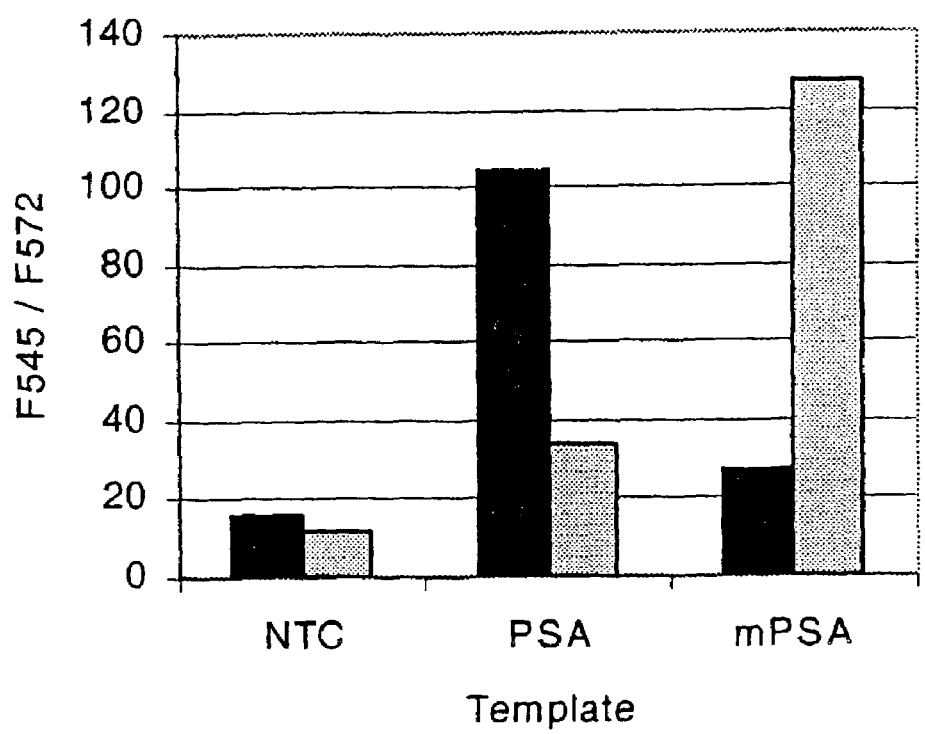

FIG. 2B shows that this signal increase is indeed due to probe cleavage. The addition of a DNA binding dye that is excited at terbium's maximum emission wavelength results in a clear terbium fluorescence decrease in reactions that did not contain a target complementary to the probe. Also, in the negative reactions, the sensitized long lived emission of the DNA binding dye is detectable at 572 nm. The shifting in emission intensities can be illustrated by dividing the emission signal at 545 nm by the signal at 572 nm. The ratio is about a tenfold greater in reactions that did contain a target complementary to the probe indicating detachment of the label from the probe in these reactions.

Real Time Quantitative PCR

Figure 3A:
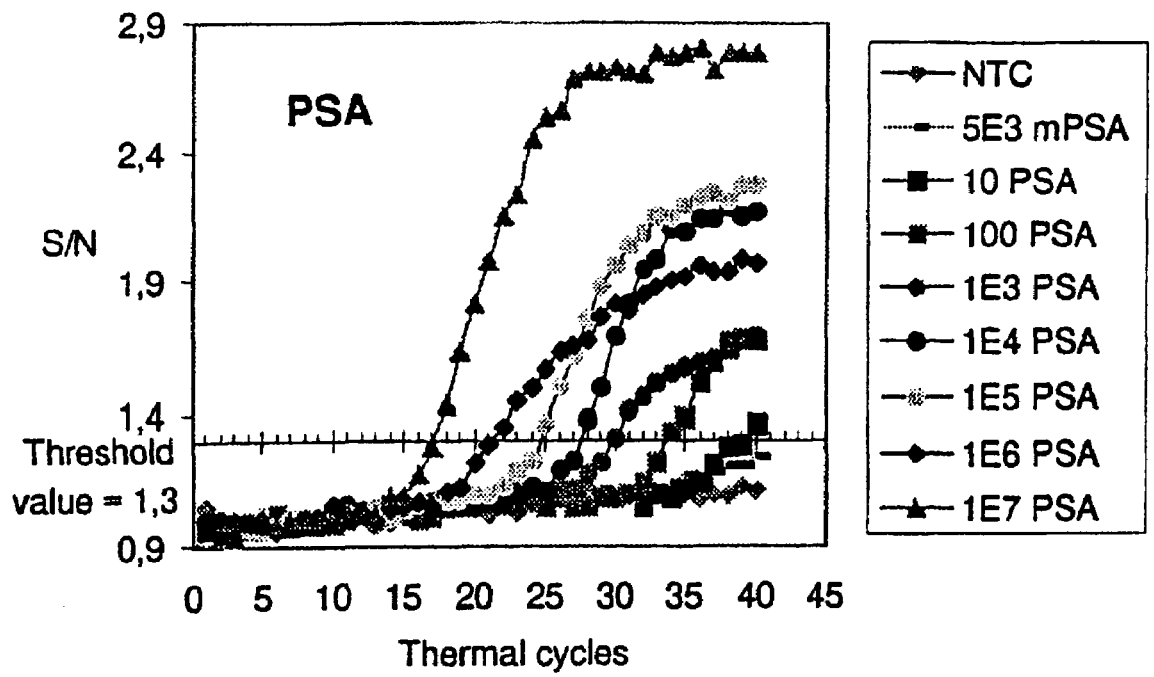
FIGS. 3A and 3B demonstrate real time monitoring of PSA and mPSA amplifications. The reactions contained either a PSA (3A) or a mPSA (3B) specific Tb labeled probe and 0-$10^7$ molecules of the respective target. Terbium fluorescence rises above background when the amount of synthesized target exceeds the detection limit of the assay. The position of the x axis shows the threshold value of each assay (1.3 in the PSA and 1.35 in the mPSA assay).
Figure 3B:
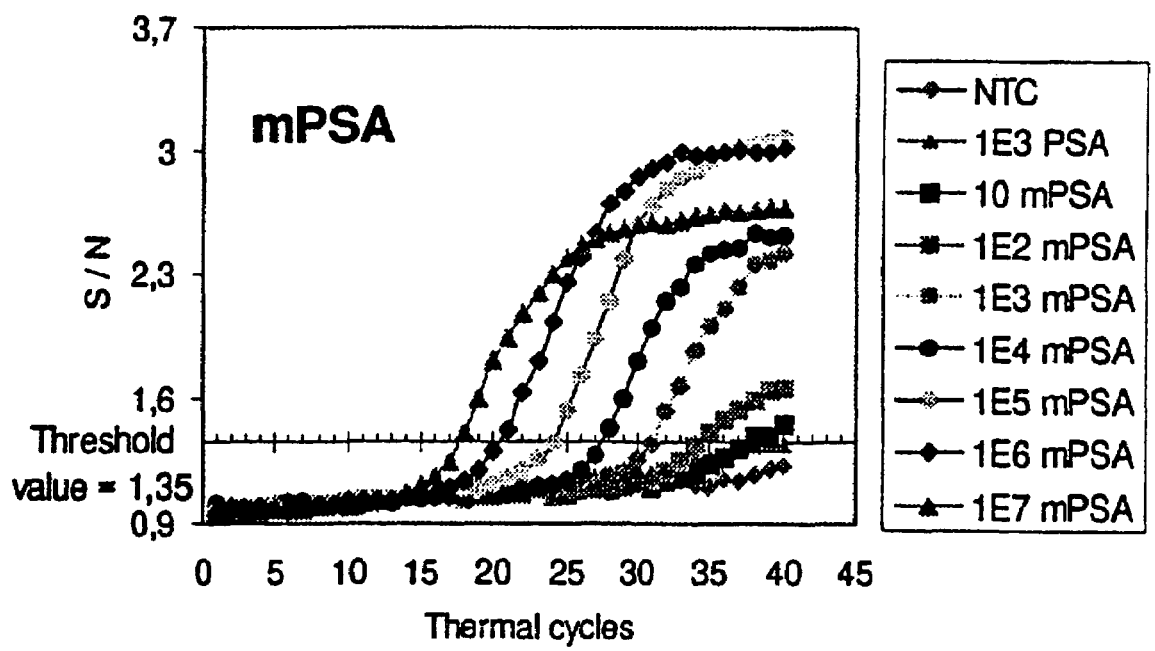
Figure 4A:
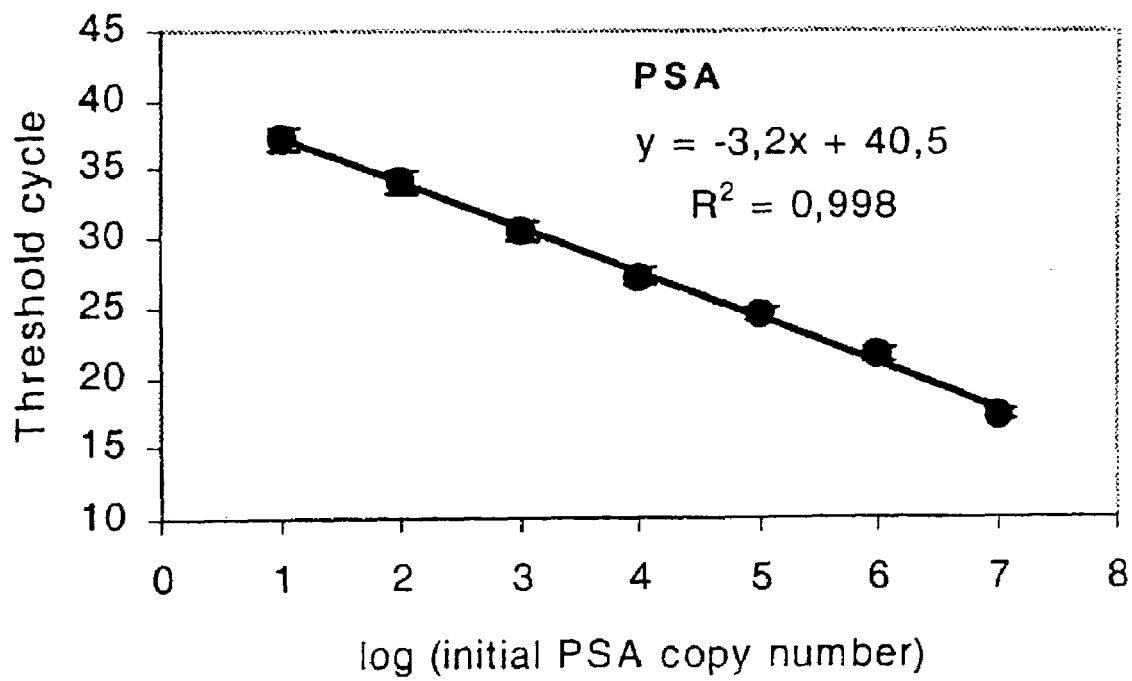
FIGS. 4A and 4B show PSA (4A) and mPSA (4B) standard curves. Threshold cycles were determined at initial template amounts ranging from 10 to $10^7$ molecules.
Figure 4B:
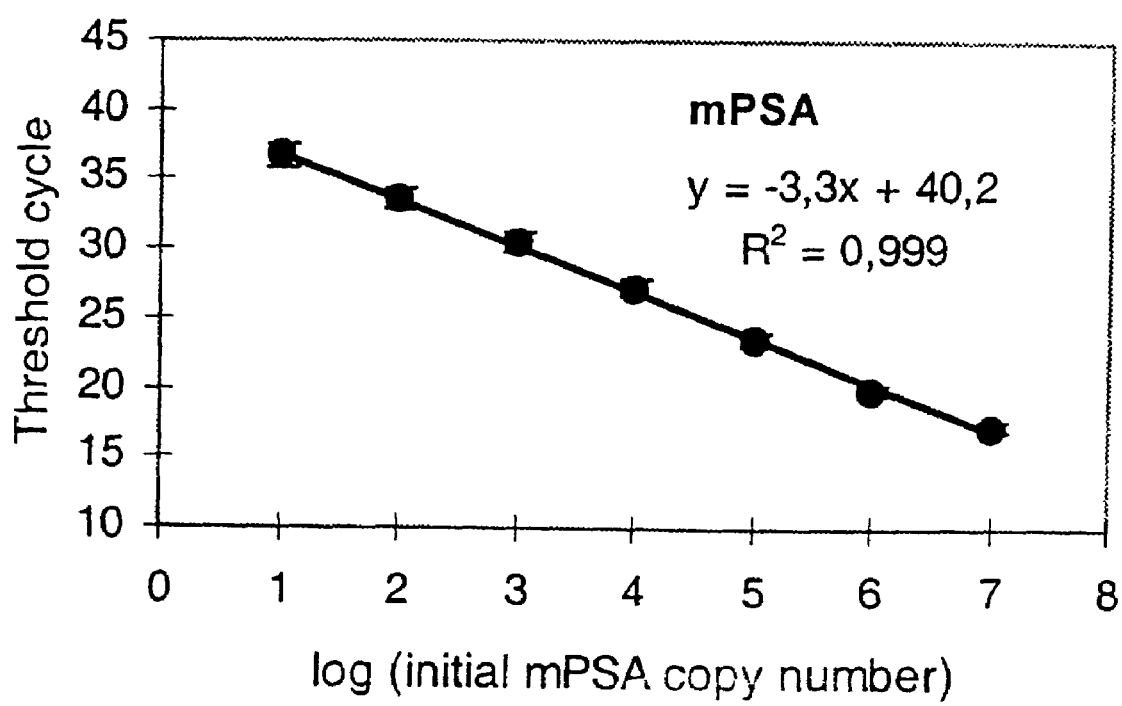

The amplification plots for different amounts of PSA and mPSA CDNA are shown in FIG. 3. The signals have been converted to signal-to-noise ratios. The noise value was determined individually for each reaction by calculating the average terbium signal of cycles 6 to 10. A threshold value to indicate the difference between positive and negative reactions was set at S/N 1.3 for the PSA and 1.35 for the mPSA assay. A higher threshold value had to be used in the mPSA assay because of a slight cross reactivity between the MPSA probe and PSA target at the annealing temperature that was used. The $C_t$:s were plotted as a function of the initial target copy number to make standard curves for each assay (FIG. 4). There is a very precise inverse log-linear relationship between the amount of starting copy number and the threshold cycle in both assays. The average coefficient of variation in replicate measurements was 2.3 (±2.5) %.

Dual End Point Assay

Figure 5:
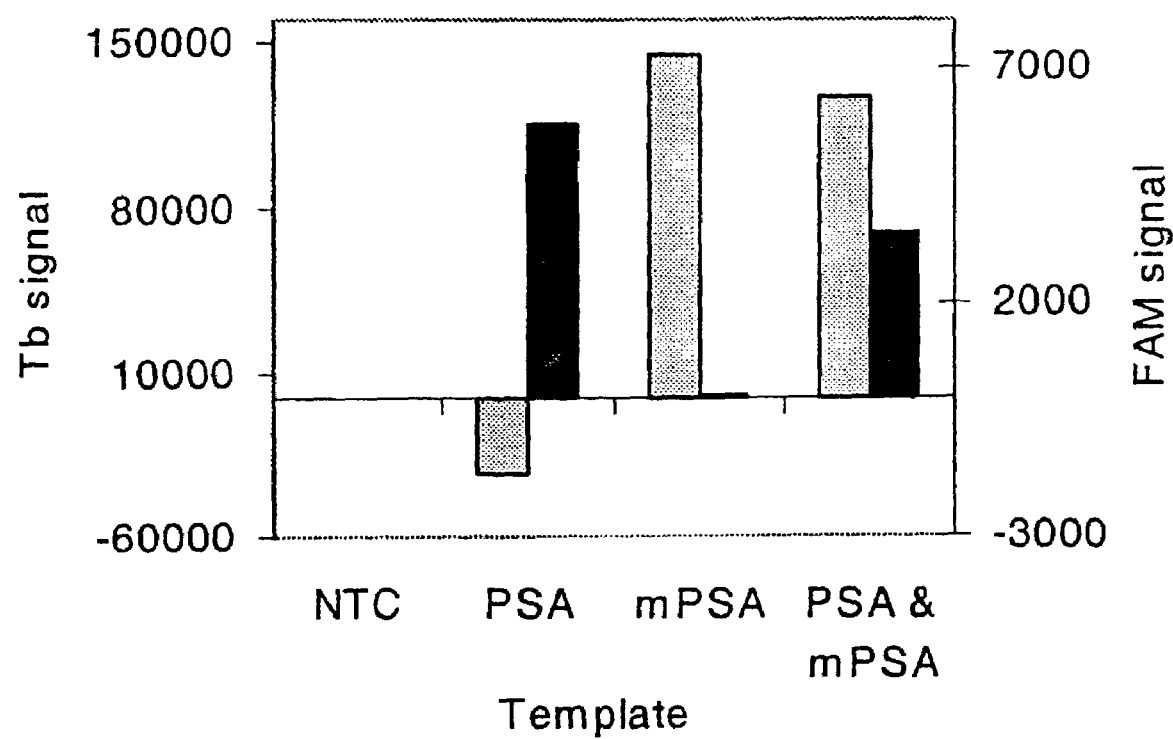
FIG. 5 shows a dual end point assay. 1000 copies of PSA, mPSA or both double stranded cDNAs were amplified in the presence of a PSA specific TaqMan probe and a mPSA specific Tb probe. Black and grey columns represent the background subtracted FAM and terbium signals, respectively, after 40 PCR cycles. There is no cross talk between the two labels: a positive FAM signal (>260 counts) is detected only in the presence of a PSA target and a positive Tb signal (>46500 counts) in the presence of a mPSA target. All reactions contained 250 ng of human genomic DNA.

Time resolved fluorometry and labels with prompt fluorescence were combined in a model assay that detects PSA and mPSA separately in one tube. FIG. 5 shows the background subtracted FAM and terbium fluorescence signals (specific for PSA and mPSA, respectively) of reactions that contained 1000 initial copies of PSA, MPSA or both together. The signals were measured after 40 PCR cycles. Threshold values (mean of negative controls+2*SD) for FAM and terbium were 260 and 46500 counts, respectively. The assay gives correct results (a positive FAM signal in the presence of PSA and a positive terbium signal in the presence of mPSA) even when the target molecules are mixed with a large excess of unspecific DNA.

Discussion

Multiple techniques exist that allow simultaneous nucleic acid amplification and detection in a closed tube (Tyagi et Kramer, 1996; Nazarenko et al., 1997; Morrison, 1995; Whitcombe et al., 1999). All these techniques need either a dual label probe or primer or two separate probes labeled with an energy transfer couple. Despite the possibility to couple several different kinds of label moieties into a probe during automated oligonucleotide synthesis, the synthesis of such dual label probes is still somewhat difficult. Since any probe impurities easily lead to a high fluorescence background and reduced assay performance, there is a need for a more straightforward approach. Although one can avoid the problems associated with dual label probes by designing two probes as in the Hybridization Probe format, this is not an ideal solution. The more probes one has to use per each target, the more complex the amplification reaction becomes and undesired artifacts, such as probe-primer dimers etc. may accumulate (Kreuzer et al., 1999). Ideally, one would only have to design one linear probe with one label and with no extra secondary structures that might interfere with probe hybridization efficiency. The detection limit of such a method should not, however, be any higher than in the existing methods where one can easily reach a linear range of at least $10$-$10^7$ molecules of initial template, when real-time detection is used in conjunction with target amplification.

We have described a label system that does not require a separate quencher moiety, since the mere proximity of single stranded DNA quenches the time-resolved fluorescence of the reporter label. The probe has the simplest possible design since no extra secondary structures are needed, either. Signal generation is based on enzymatic, template dependent probe cleavage. Cleavage of the probe results in a signal increase that can be used for qualitative and quantitative detection of a target nucleic acid in a homogeneous solution. A maximum signal-to-noise ratio of 4 was obtained by digesting a terbium labeled probe with a nuclease. Although this signal increase is quite modest when compared to results obtained with for example molecular beacon probes (Tyagi et al., 1998), it is however sufficient: a large dynamic range (at least $10$-$10^7$ molecules of initial template) was obtained. This is probably due to the fact that in a time resolved fluorescence measurement the unspecific background fluorescence is almost insignificant (Soini et Lovgren, 1987) and therefore very subtle changes in the specific signal can be detected. The actual detection limit of a real time PCR assay refers to the number of target amplicons synthesized when a detectable fluorescence signal occurs. An estimation of this detection limit can be obtained by extrapolating a standard curve to the point where $C_t$=0. With our detection technology this detection limit is about $10^{12}$ synthesized target amplicons, which is very similar to results obtained with other techniques (Nitsche et al., 1999; Vet et al., 1999). It is possible that this detection limit can be further improved by increasing the labeling degree of the probe and/or by optimizing the position of the label moiety in the probe. Further studies are also needed to determine the effect of probe sequence to the quenching efficiency.

We had to label our probes following synthesis because a phosphoramidite that would enable direct coupling of the chelate to the probe during synthesis does not exist. Different chelates have, however, been derivatized into phosphoramidites (Kwiatkowski et al., 1994). Therefore, we assume that a phosphoramidite reagent that would contain the chelate that was used in this study is feasible. Once such a reagent is available, probe synthesis will be simplified even further.

The benefits of real time quantitative PCR (Higuchi et al., 1992) have been widely described (Orlando et al., 1998; Freeman et al., 1999). These include improved reproducibility, reduced contamination risks and higher assay throughput when compared to traditional quantitative PCR assays that include several post PCR steps. Quantitative PCR assays based on end point determination of the amount of PCR product are not only laborious but reliability of results is often questionable because the amount of PCR product at the end of thermal cycling is only poorly correlated to the amount of initial template (FIG. 3). However, determination of the threshold cycle (the point of time when enough PCR product has been synthesized for a detectable fluorescence signal to occur) enables a very precise and reproducible quantification, because detection is done before the amplification reaction reaches a plateau phase.

Currently, all available homogeneous nucleic acid detection methods employ labels with rapidly decaying or prompt fluorescence. Because of the wide, overlapping emission peaks of the labels used, multiparametric measurements always require the use of powerful spectral resolution software, i.e. the results cannot be read directly from the fluorescence counts at different wavelengths. But even with the best software it is sometimes impossible to distinguish the emissions of two labels from one another, which may result in false positive results (Vet at al., 1999). A better approach would be the use of fluorescent labels with long excited state lifetimes (such as stable, fluorescent lanthanide chelates) and time-resolved fluorometry (Soini et Lovgren, 1987) together with prompt labels. In a time-resolved fluorescence measurement the signal is not recorded straight after the excitation pulse but after a certain delay. During this delay unspecific background fluorescence and fluorescence from any prompt labels, such as fluorescein, disappear. The measurement is repeated several times during a short period of time, which results in a signal amplification. Since lanthanides are excited by light in the UV range, they do not cause any background signal for prompt labels that are excited by light in the visible range. Therefore, by combining these label technologies in one assay one can totally discriminate between the signals coming from different labels and maximize the specificity of a homogeneous multi-analyte assay. In this study we detected two very similar analytes separately in one tube. This was done to demonstrate that by combining labels with different fluorescence lifetimes one can achieve multi-analyte systems that do not suffer from any cross talk between labels. The emission spectra of the labels that were used (Tb and FAM) overlap considerably. However, their signals were completely resolved from each other. We expect it to be fairly straightforward to increase the number of analytes in one tube further without compromising assay specificity by choosing labels with different fluorescence lifetimes and different excitation wavelengths and by using a variable-wavelength excitation light source in the measurements.

In addition to allele discrimination and other qualitative assays, the possibility to do multiplex detection is of importance to quantitative assays as well. Despite the fact that an internal standard is not needed to compensate for the changes in amplification efficiency when quantification is based on real-time detection (McBride et al., 1998), an internal standard is still needed to compensate for the errors coming from sample processing and possible reverse transcription steps (Freeman et al., 1999). The best way to quantify the internal standard, in terms of assay throughput, simplicity and reliability, is in the same tube with the actual target. We have shown this approach to be feasible by detecting PSA and mPSA, an internal standard that is amplified by the same primers as PSA, in one sealed tube.

We have demonstrated the applicability of this new signal generation principle to both quantitative and qualitative nucleic acid assays. Although a qualitative assay is not needed for our model analytes, PSA CDNA and an in vitro produced mutant form of PSA, their detection in the presence of a large excess of unrelated DNA shows that our label technology can be applied to various kinds of mutation or pathogen detection systems. We conclude that by using a probe labeled at its 5' end with a stable, fluorescent terbium chelate one can easily construct a nucleic acid assay that is as user friendly and reliable as other corresponding methods with the additional attributes of simpler probe design and a far better suitability to multiplex assays.

Study II

Hybridization Dependent Terbium Signal Increase

Description of the Experiments

An oligonucleotide probe with the base sequence 5'-CCT TCT GAG GGT GAA CTT GCG C (SEQ ID NO:5)-C7-3' was modified with a 5'-Amino Modifier C6-TFA and a 3'-Amino Modifier C7 (Glen Research Corporation, Sterling, USA). The probe was labelled with 2,2',2'',2'''-{{6,6'-{4''-{2-{4-{[2-(4-isothiocyanatophenyl)-1-oxo-ethyl]amino}phenyl}ethyl}-1H-pyrazole-1'',3''-diyl} bis(pyridine)-2,2'-diyl}bis(methylenenitrilo)} tetrakis(acetato) terbium(III) and separately with 2,2',2'',2'''-{{6,6'-{4''-[2-(4-isothiocyanatophenyl)ethyl]-1H-pyrazole-1'',3''-diyl}bis(pyridine)-2,2'-diyl}bis(methylenenitrilo)}tetrakis(acetato) terbium(III). The probes (Tb1093 and Tb1093S, respectively) containing a Tb label at both ends were HPLC purified from uncoupled label and probe.

The probes Tb1093 and Tb1093S were tested in a homogeneous hybridization with a synthetic target oligonucleotide having the sequence 5'-G CGC AAG TTC ACC CTC AGA AGG-3' (SEQ ID NO:6). $10^{10}$ molecules of the Tb labelled probe were mixed with $10^8$, $10^9$, $10^{10}$, $10^{11}$ and $10^{12}$ molecules of the target oligonucleotide in 50 μl of a hybridization buffer containing 100 mM Tris-HCl pH 7.5; 250 μM EDTA; 1 M NaCl; 0.1% Tween 20; 10% PEG 8000; 250 μg μl$^{-1}$ bovine serum albumin. The terbium signals were recorded immediately after mixing at 545 nm (excitation wavelength 340 nm, flash energy level 173, delay time 500 μs, window time 1400 μs, cycle time 2000 μs) using a Victor™ 1420 Multilabel Counter (PerkinElmer Life-Sciences, Turku, Finland). The signals from hybridization reactions containing the synthetic target were compared to negative controls containing no target.

The hybridization dependence of the terbium signal increase was demonstrated by mixing $10^{10}$ molecules of the terbium labelled probes with a tenfold molar excess of the specific target sequence. The probe Tb1093 was also mixed with a tenfold molar excess of non complementary single stranded DNA or 1 µg of unrelated double stranded plasmid DNA. The terbium signals of all mixtures were recorded as described above and the signals were compared to negative controls containing only the Tb labelled probe.

The probe Tb1093 was also tested in the detection of a specific polymerase chain reaction product. A 163 bp segment of prostate specific antigen CDNA was amplified in the presence of the probe using a 5'-exonuclease deficient DNA polymerase. The 50 µl reactions consisted of 1× AdvanTaq PCR Buffer (Clontech Laboratories, Palo Alto, USA); 3.5 mM $MgCl_2$; 0.2 mM dNTP:s; 0.5 µM forward primer (sequence 5'-TGA ACC AGA GGA GTT CTT GAC-3'; SEQ ID NO:1); 60 nM reverse primer (5'-CCC AGA ATC ACC CGA GCA G-3'; SEQ ID NO:2); $10^{10}$ molecules of the terbium labelled probe and 1× AdvanTaq DNA Polymerase (Clontech Laboratories). The thermal cycling was performed in a PTC200 DNA Engine (MJ Research, USA) as follows: initial denaturation at 94° C. for 2 min 30 s and 40 cycles of denaturation at 94° C. (30 s), annealing at 61.5° C. (30 s) and extension at 68° C. (45 s) after which the reactions were cooled to 25° C. and the terbium signals were recorded from each amplification well as described above. The signals from reactions that contained $5*10^6$ molecules of PSA double stranded cDNA were compared to signals obtained from negative control reactions. The terbium probe is complementary to the extension product of the forward primer. The amplification was made asymmetric (an approximately eight fold excess of forward primer was used when compared to the amount of the reverse primer) to ensure that at the measurement temperature (room temperature) there would be enough single stranded product available for hybridization.

Results

Figure 6:
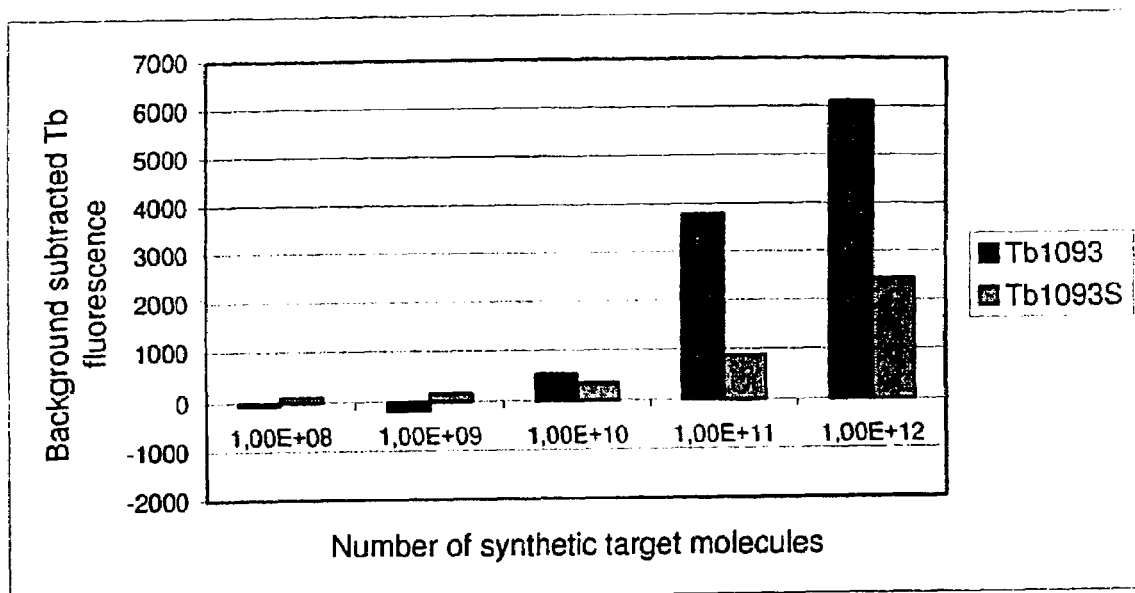
FIG. 6 shows the hybridization dependent Tb signal increase of oligonucleotide probes labelled at both ends with a stable, fluorescent, environment-sensitive Tb chelate. The background subtracted terbium signals (background being the average terbium fluorescence of negative controls+1.96*standard deviation) are shown. $10^{10}$ synthetic target molecules give a clearly positive signal. Black and grey columns denote the signals obtained from probes labelled with different chelates; Tb1093 and Tb1093S, respectively (see Experimental Section, Study II, for details).

Hybridization of the Tb labelled probes with a complementary target sequence resulted in a clear terbium signal increase. FIG. 6 shows the background subtracted terbium signals of hybridization reactions containing $10^{10}$ molecules of the terbium labelled probe and different amounts of a complementary target oligonucleotide. $10^{10}$ molecules of the target are needed to generate a signal that is significantly above background.

Figure 7:
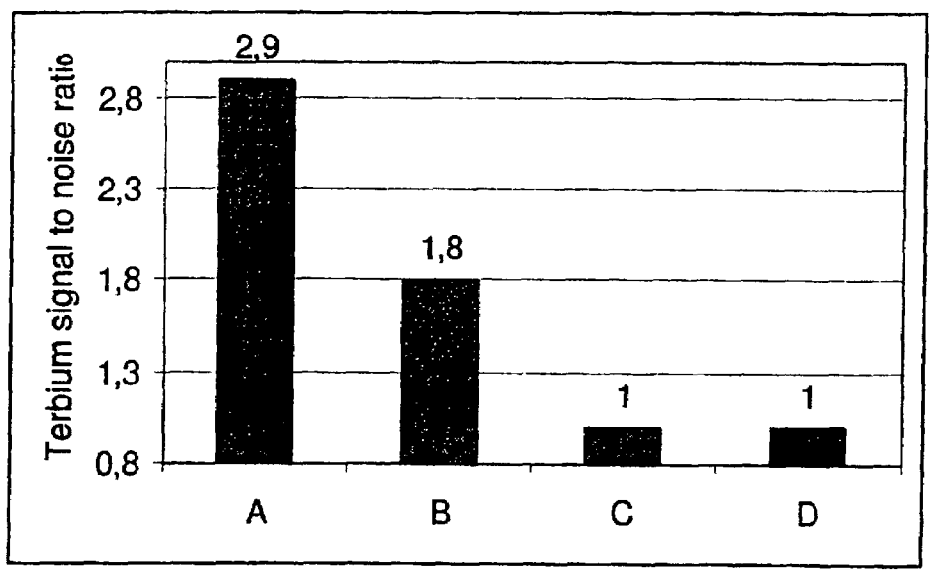
FIG. 7 shows the specificity of the hybridization dependent lanthanide signal increase. A=Tb1093S+complementary target; B=Tb1093+complementary target; C=Tb1093+non complementary single stranded DNA; D=Tb1093+unrelated double stranded DNA. Only the presence of a complementary nucleic acid results in lanthanide fluorescence increase. The maximum signal to noise ratios for the probe Tb1093S, when the measurement parameters described in the experimental section are used, is 2.9 and for the probe Tb1093 1.8. The noise is defined as the terbium signal obtained from a mixture that does not contain other nucleic acid than the Tb labelled probe. The presence of non complementary single or double stranded DNA does not have an effect on terbium fluorescence intensity.
Figure 8A:
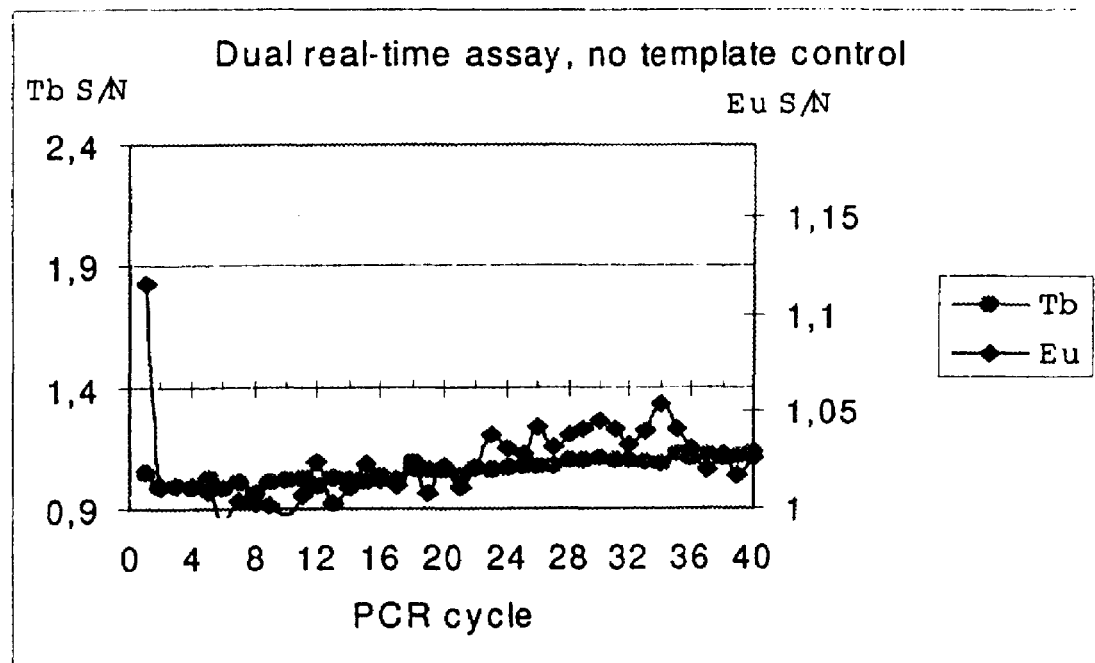
FIGS. 8A to 8D show how two probes, one of which is labelled with an environment-sensitive terbium and the other with a europium chelate, can be used in the detection of two different nucleic acid target sequences in one single tube.
Figure 8B:
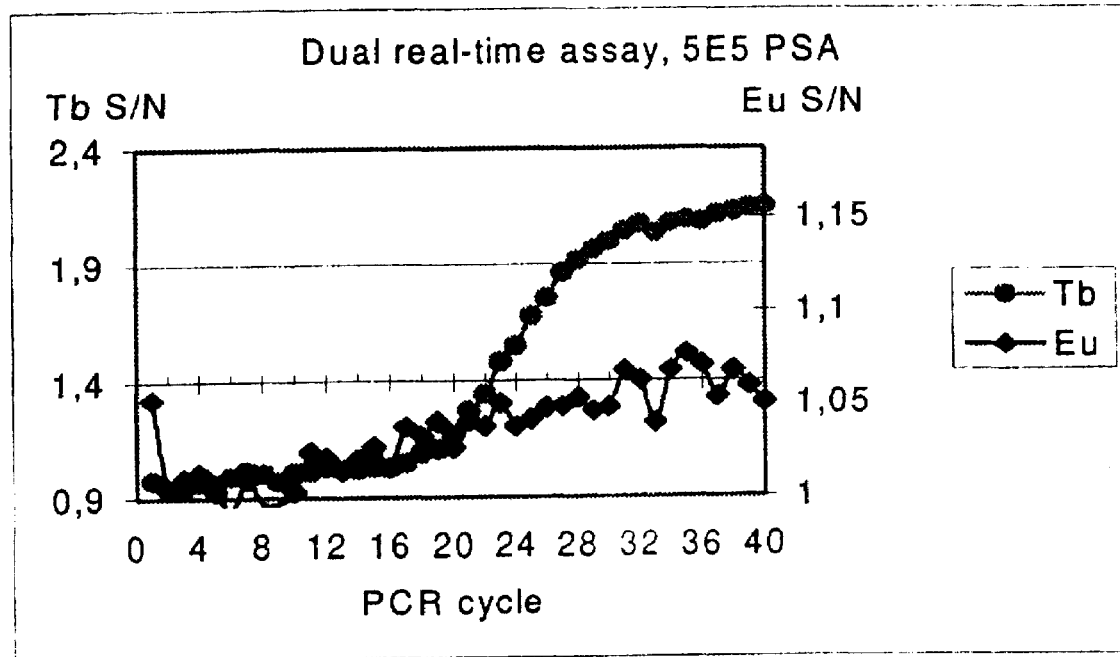
Figure 8C:
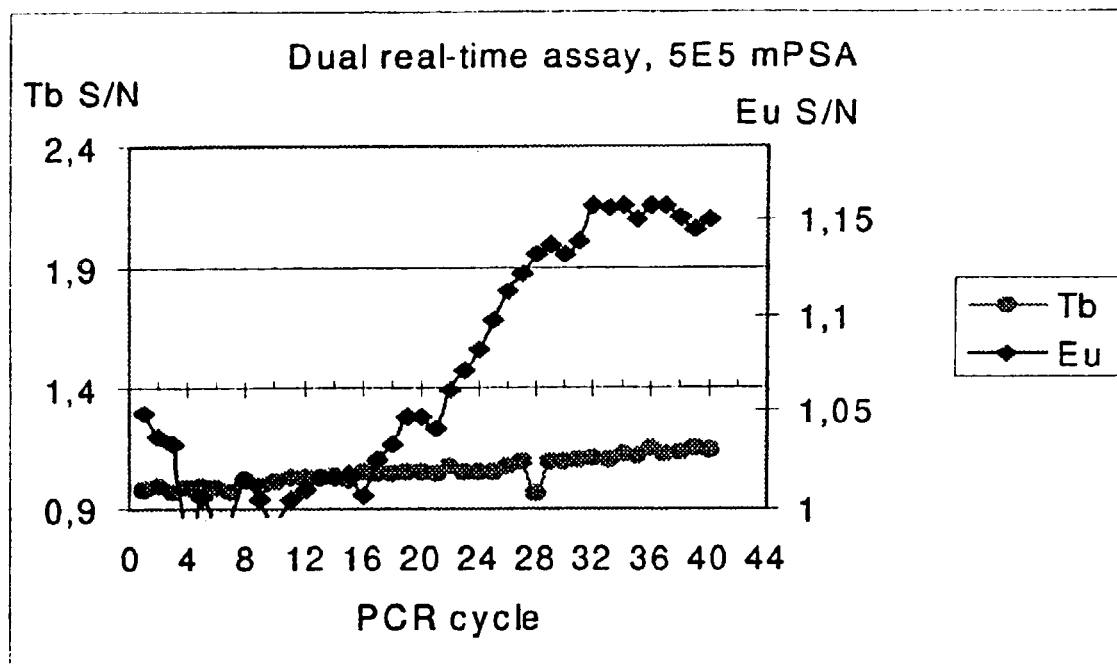
Figure 8D:
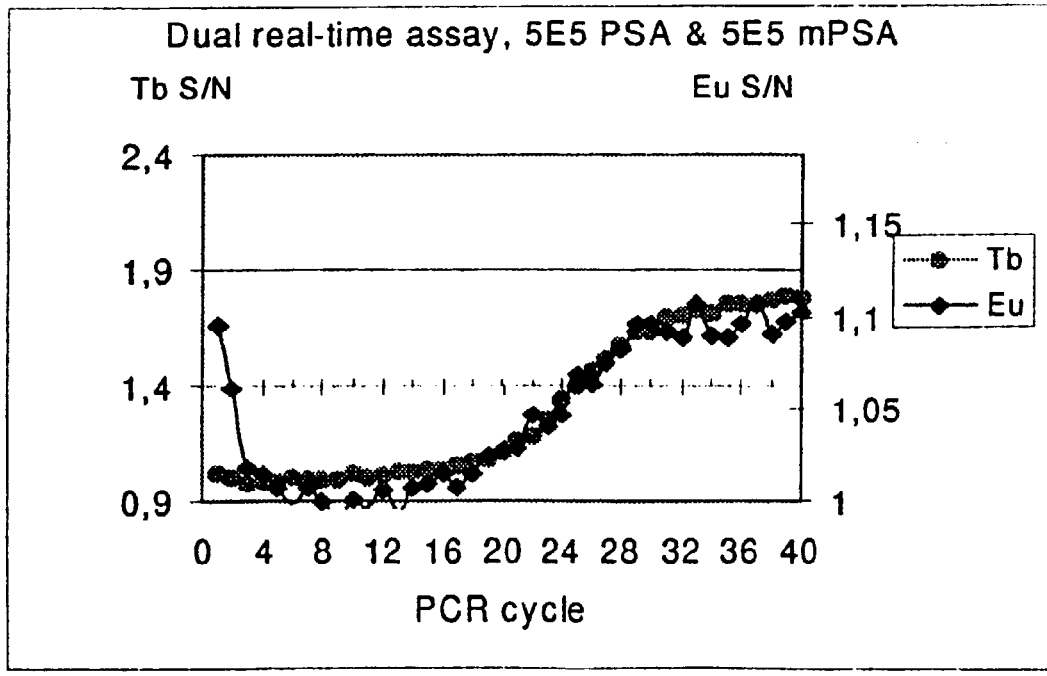

The fact that this signal increase is indeed due to hybridization and not some other artifact was shown in an experiment, where the terbium probe was mixed with its complementary target and unspecific single or double stranded DNA. The results are shown in FIG. 7. Only the presence of a complementary target results in a terbium signal increase.

The probe Tb1093 was used in the detection of a specific polymerase chain reaction product. The amplification reaction was made asymmetric by using an eight fold excess of the primer the extension product of which is complementary to the Tb labelled probe. The DNA polymerase that was used is a 5'-exonuclease-deficient enzyme, so the probe is not degraded by the polymerase during PCR. Any terbium signal increase must therefore be a result of hybridization and not probe cleavage. The positive reactions that contained a PSA CDNA template gave, when the terbium signals were recorded after amplification, a fluorescence signal that was 472 counts above a threshold value that was the average fluorescence of negative control reactions+ 1.96*standard deviation of the negative controls. This clearly indicates that oligonucleotide probes labelled with an environment-sensitive lanthanide chelate can be used in the detection of a specific polynucleotide in a closed tube.

Study III

Multiplex Detection of Two Different Target Nucleic Acids Using Probes Labelled with Europium and Terbium Description of the Experiment The mPSA specific probe (table 1, Study I) was labelled with 2,2',2",2"'∝1-{{6,6'-{4"-[2-(4-isothiocyanatophenyl) ethyl]-1H-pyrazole-1",3"-diyl} bis(pyridine)-2,2'-diyl}bis (methylenenitrilo)}tetrakis(acetato) europium(III). The probe was used together with the terbium labelled PSA specific probe (table 1) in real-time detection of PSA or/and MPSA amplification. The amplifications were done in conditions that were equal to those described in Study I under the headline "Real time quantitative PCR" except that this time both the terbium labelled PSA specific probe and the europium labelled mPSA specific probe were included in the reaction, both at a concentration of 33 nM. The terbium and europium signals were measured at the end of each annealing step. The terbium measurement parameters were as described above. In the europium measurement, the excitation wavelength was 340 nm. Time-resolved emission light was collected at 615 nm using a delay time of 200 µs and a time window of 1800 µs. The cycle time was 2100 µs. The europium signals were corrected for terbium background, because one of terbium's emission maxima is at 615 nm. The spectral correction was done by subtracting from the measured europium signal the terbium signal measured at 545 nm multip lied by 0.24. All signals were divided by the average fluorescence of cycles 6 to 10 to generate signal to noise ratios. The individual amplification reactions contained either no template, $5*10^5$ molecules of PSA or mPSA double stranded DNA or equal amounts of both templates.

Results

The europium and terbium signal to noise ratios obtained from reactions containing a europium labelled mPSA probe, a terbium labelled PSA probe and no template or PSA or/and mPSA template are shown in FIG. 8. The amplification of PSA double stranded cDNA results in a terbium signal increase, whereas the amplification of mPSA results in a europium signal increase. These results show that two lanthanide labels can be used in a multiplex homogeneous nucleic acid assay, the signal intensity of each label indicating the presence or absence of the respective target polynucleotide.

It will be appreciated that the methods of the present invention can be incorporated in the form of a variety of embodiments, only a few of which are disclosed herein. It will be apparent for the specialist in the field that other embodiments exist and do not depart from the spirit of the invention. Thus, the described embodiments are illustrative and should not be construed as restrictive.

REFERENCES

Clegg, R. M. (1992) *Meth Enzymol.,* 211, 353-388

Freeman, W. M., Walker, S. J. and Vrana, K. E. (1999) *Biotechniques* 26, 112-122; 124-125

Higuchi, R., Dollinger, G., Walsh, P. S. and Griffith, R. (1992) *Bio/Technology* 10, 413-417

Holland, P. M., Abramson, R. D., Watson, R. and Gelfand, D. H. (1991) *Proc Natl Acad Sci USA.* 88, 7276-7280

Isaksson, A. and Landegren, U. (1999) *Curr Opin Biotechnol.* 10, 11-15

Kreuzer, K. A., Lass, U., Bohn, A., Landt, O. and Schmidt, C. A.(1999) *Cancer Res.* 59, 3171-3174

Kricka, L. J.(1999) *Clin Chem.* 45, 453-458

Kwiatkowski, M., Samiotaki, M., Lamminmaki, U., Mukkala, V. M. and Landegren, U. (1994) *Nucl Acids Res.* 22, 2604-2611

Latva, M., Takalo, H., Mukkala, V.-M., Matachescu, C., Rodriguez-Ubis, J. C. and Kankare, J. (1997) Correlation between the lowest triplet state energy level of the ligand and lanthanide(III) luminescence quantum yield. In Latva, M., Studies on the solution structure, energy transfer and enhanced luminescence of Eu(III) and Tb(III) aminopolycarboxylate chelates, Academic dissertation. Department of Chemistry, University of Turku, Finland.

Lee, G. L., Connell, C. R. and Bloch, W. (1993) *Nucleic Acids Res.* 21, 3761-3766

Livak, K., Flood, S., Marmaro, J., Giusti, W. and Deetz, K. (1995) *PCR Meth Appl.* 4, 357-362

Lundwall, Å. and Lilja, H. (1987) *FEBS Lett.* 214, 317-322

Lövgren, T. and Pettersson, K. (1990) Time-resolved fluoroimmunoassay, advantages and limitations. In Van Dyke, K. (ed.), *Luminescence immunoassay and molecular applications*. CRC Press, Boca Raton, Fla., 233-250

McBride, L., Livak, K., Lucero, M., Goodsaid, F., Carlson, D., Stevens, J., Allen, T., Wyatt, P., Thiel, D., Honebein, P. et al. (1998) In Ferré, F. (ed.), *Gene quantification*. Birkhäuser, Boston, 97-110

Morrison, L. E. (1995) In Kricka, L. J. (ed.), Nonisotopic probing, blotting, and sequencing. Academic Press, Inc., San Diego, 430-471

Mukkala, V.-M., Helenius, M., Hemmila, I., Kankare, J. and Takalo, H. (1993) Development of luminescent europium (III) and terbium(III) chelates of 2,2':6',2"-terpyridine derivatives for protein labelling. *Helv. Chim. Acta* 76

Nazarenko, I. A., Bhatnagar, S. K. and Hohman, R. J. (1997) *Nucleic Acids Res.* 25, 2516-2521

Nitsche, A., Steuer, N., Schmidt, C. A., Landt, O. and Siegert, W. (1999) *Clin Chem.* 45, 1932-1937

Orlando, C., Pinzani, P. and Pazzagli, M. (1998) *Clin Chem Lab Med.* 36, 255-269

Saiki, R. K., Scharf, S., Faloona, F., Mullis, K. B., Horn, G. T., Erlich, H. A. and Arnheim, N. (1985) *Science* 230, 1350-1354

Selvin, P. R. (1995) *Meth EnzymoL* 246, 300-334

Soini, E. and Lövgren, T. (1987) *CRC Crit Rev Anal Chem.* 18, 105-154

Takalo, H., Mukkala, V.-M., Meriö, L., Rodriguez-Ubis, J. C., Sedano, R., Juanes, O. and Brunet, E. (1997) Development of luminescent terbium(III) chelates for protein labelling: effect of triplet-state energy level. *Helv Chim Acta* 80, 372-387

Tyagi, S. and Kramer, F. R. (1996) *Nature Biotechnology* 14, 303-308

Tyagi, S., Bratu, D. P. and Kramer, F. R. (1998) *Nature Biotechnology* 16, 49-53

Vet, J. A. M., Majithia, A. R., Marras, S. A. E., Tyagi, S., Dube, S., Poiesz, B. J. and Kramer, F. R. (1999) *Proc Natl Acad Sci USA.* 96, 6394-6399

Whitcombe, D., Theaker, J., Guy, S. P., Brown, T. and Little, S. (1999) *Nat Biotechnol.* 17, 804-807

Williams, P. M., Giles, T., Tucker, A., Winer, A. and Heid, C. (1998) In Ferré, F. (ed.), *Gene quantification*. Birkhäuser, Boston, 313-325

Wittwer, C. T., Herrman, M. G., Moss, A. A. and Rasmussen, R. P (1997a) *Biotechniques* 22, 130-131; 134-138

Wittwer, C. T., Ririe, K., Andrew, R., David, D., Gundry, R, and Balis, U. (1997b) *BioTechniques* 22, 176-181

Ylikoski, A., Sjoroos, M., Lundwall, A., Karp, M., Lovgren, T., Lilja, H. and Iitiä, A. (1999) *Clin Chem.* 45, 1397-1407

---

The invention claimed is:

1. A homogenous method for detecting at least one target polynucleotide in a sample comprising the steps of
contacting a sample, comprising said polynucleotide with an oligonucleotide probe labeled with a label under conditions where said oligonucleotide probe selectively hybridizes to said target polynucleotide, wherein the signal of the label itself increases or decreases upon the hybridization of the oligonucleotide probe and the target polynucleotide, and the label consists of a fluorescent lanthanide chelate,
exciting the label, and
without removing unhybridized probes, monitoring the signal intensity of said label by time resolved fluorometry to indicate the presence or absence in a sample of said target polynucleotide.

2. The method according to claim 1, wherein the sample is contacted with additional oligonucleotide probes having different base sequences, said probes being labeled with different labels so that all labels have distinguishable signal wavelengths, said additional oligonucleotide probes thus being able to hybridize to different target polynucleotides in the sample.

3. The method according claim 1, wherein the method is carried out in the real-time monitoring of nucleic acid synthesis reactions by measuring the signal intensity of said label at regular intervals during a nucleic acid synthesis reaction and comparing the signal intensities of a reaction containing a sample of nucleic acids and of a negative control reaction that does not contain said target polynucleotide, a difference in the signal intensities of these two indicating the presence of said target polynucleotide in said sample; and detecting the point of time when the signal intensity of a reaction containing said target polynucleotide clearly starts to differ from the signal intensity of said negative control reaction, the detected point of time indicating the initial amount of said target polynucleotide in said sample.

4. The method according to claim 1, wherein the method is carried out in the end-point detection of nucleic acid synthesis reaction products by measuring the signal intensity of said label after said nucleic acid synthesis reaction and comparing the signal intensity of a reaction containing said sample of nucleic acids and the signal intensity of a negative control reaction that does not contain said target polynucleotide, a difference in the signal intensities of these reactions indicating the presence of said target polynucleotide in said sample of nucleic acids.

5. The method according to claim 1, where said oligonucleotide probe is made of DNA, RNA, peptide nucleic acid (PNA), or a chimera thereof.

6. The method according to claim 1, wherein said target polynucleotide is a single stranded nucleic acid, DNA or RNA, or a double stranded stretch of DNA or RNA.

7. The method according to claim 1, wherein said label is attached to the 5' terminal nucleotide of said oligonucleotide probe.

8. The method according to claim 1, wherein said label is attached to the 3' terminal nucleotide of said oligonucleotide probe.

9. The method according to claim 1, wherein said label is attached to the 5' and 3' terminal nucleotides of said oligonucleotide probe.

10. The method according to claim 1, wherein said label is attached to any nucleotide of said oligonucleotide probe between 5' and 3' terminal nucleotides.

11. A method of determining the presence of a target nucleic acid sequence in a sample, comprising the steps of
providing a mixture of
   a sample of interest, and
   a nucleic acid probe comprising a nucleic acid sequence selectively binding said target nucleic acid sequence and one or more labels wherein the one or more labels consist of fluorescent lanthanide chelates,
wherein each of said fluorescent lanthanide chelate is capable of changing the intensity of its own fluorescence emission upon hybridization of said probe to said target nucleic acid sequence,
subjecting the mixture to conditions under which the probe selectively hybridizes to the target nucleic acid, and
without removing unhybridized probes from the mixture, determining whether each fluorescent lanthanide chelate changes the intensity of its own fluorescence emission by measuring fluorescence emission from the mixture by time resolved fluorometry,
thereby determining the presence of said target nucleic acid sequence in the sample if the intensity does change over time.

12. The method of claim 1, wherein the fluorescent lanthanide chelate is terbium or europium chelates of a derivative of 2,2',2'',2'''-{[6,6'-(Pyrazole-1'',3''-diyl)bis(pyridine)-2,2'-diyl]bis(methylenenitrilo)}tetrakis (acetic acid) or 2,2':6',2''-terpyridine.

13. The method of claim 11, wherein the fluorescent lanthanide chelate is terbium or europium chelates of a derivative of 2,2',2'',2'''-{[6,6'-(Pyrazole-1'',3''-diyl)bis(pyridine)-2,2'-diyl]bis(methylenenitrilo)}tetrakis (acetic acid) or 2,2':6',2''-terpyridine.

* * * * *